(12) United States Patent  
Witt

(10) Patent No.: US 9,125,702 B2  
(45) Date of Patent: Sep. 8, 2015

(54) ACETABULAR DRILL PIN

(71) Applicant: Biomet Manufacturing Corporation, Warsaw, IN (US)

(72) Inventor: Tyler Witt, Warsaw, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 337 days.

(21) Appl. No.: 13/779,801

(22) Filed: Feb. 28, 2013

(65) Prior Publication Data

US 2014/0243831 A1  Aug. 28, 2014

(51) Int. Cl.
| | |
|---|---|
| A61B 17/56 | (2006.01) |
| A61B 17/58 | (2006.01) |
| A61B 17/60 | (2006.01) |
| A61F 2/00 | (2006.01) |
| A61F 2/30 | (2006.01) |
| A61B 17/84 | (2006.01) |
| A61B 17/17 | (2006.01) |
| A61B 17/16 | (2006.01) |
| A61B 19/00 | (2006.01) |

(52) U.S. Cl.
CPC .......... *A61B 17/848* (2013.01); *A61B 17/1746* (2013.01); *A61B 17/1615* (2013.01); *A61B 17/1684* (2013.01); *A61B 2019/462* (2013.01)

(58) Field of Classification Search
USPC .................................... 606/80, 91
See application file for complete search history.

(56) References Cited

U.S. PATENT DOCUMENTS

| | | | |
|---|---|---|---|
| 7,780,672 | B2 | 8/2010 | Metzger et al. |
| 8,070,752 | B2 | 12/2011 | Metzger et al. |
| 8,092,465 | B2 | 1/2012 | Metzger et al. |
| 8,298,237 | B2 | 10/2012 | Schoenefeld et al. |
| 2009/0024131 | A1 | 1/2009 | Metzger et al. |
| 2011/0184419 | A1* | 7/2011 | Meridew et al. ............ 606/80 |

* cited by examiner

*Primary Examiner* — Sameh Boles  
(74) *Attorney, Agent, or Firm* — Taft Stettinius & Hollister LLP; Ryan O. White

(57) ABSTRACT

An acetabular drill pin comprising an elongated shaft having a proximal end and a distal end opposite thereof along a longitudinal axis of the shaft; at least two depth markings along the shaft, each of the at least two depth markings being positioned a pre-defined distance from the distal end of the shaft; and a fluted portion proximate the distal end of the shaft, the fluted portion being disposed between a shoulder and a flat-bottom milling tip, the tip being configured to penetrate a peri-acetabular area of a pelvis as the fluted portion is imparted with rotary motion.

7 Claims, 9 Drawing Sheets

ACETABULAR DRILL PIN

TECHNICAL FIELD

The present teachings are related to an acetabular drill pin for positioning an acetabular cup during a hip procedure.

BACKGROUND OF THE DISCLOSURE

The statements in this section merely provide background information related to the present disclosure and should not be construed as constituting prior art.

Many portions of the human anatomy naturally articulate relative to one another. Generally, the articulation of these anatomic regions is smooth and non-abrasive in nature, particularly in the presence of natural tissues, such as cartilage and strong bone.

Over time, however, due to injury, stress, degenerative health problems and various other issues, the ease by which these anatomic regions are able to articulate degenerates in quality, thereby leaving the articulation of these anatomic regions abrasive and impractical. For example, injury may cause the cartilage or the bony structure to become weak, damaged, or even non-existent. As a result, the natural articulation of these anatomical regions is no longer possible for these affected individuals.

At such times, it may be desirable to replace the affected anatomical regions with a prosthetic component so that normal articulation may be restored. As part of this process, it may become necessary to replace the acetabulum with a prosthetic component if its articulation with the proximal femur becomes rough, abrasive or damaged. To assist the operating surgeon accurately install the acetabular cup in the acetabulum in accordance with a pre-operatively defined orientation, a patient-matched acetabular cup placement guide may be used. To secure the patient-matched placement guide to the acetabulum, traditional procedures sometimes utilize a trocar tip pin (e.g., a Steinmann pin). As these pins encounter the surface of the acetabulum, the acute angle of insertion can cause the pin to deflect off the acetabular surface, thereby causing an inaccurate translation of the placement guide's position. As a result, a high level of variability exists in terms of accurately placing the cup in line with its targeted pre-operatively planned orientation.

What is needed then is an improved pin that can more securely engage the bony surface surrounding the acetabulum. The present application is intended to improve upon and resolve some of these known deficiencies of the art.

SUMMARY OF THE DISCLOSURE

In accordance with one aspect of the present application, an acetabular drill pin is provided. In accordance with this aspect of the present disclosure, the drill pin comprises an elongated shaft having a proximal end and a distal end opposite thereof along a longitudinal axis of the shaft; at least two depth markings along the shaft, each of the at least two depth markings being positioned a pre-defined distance from the distal end of the shaft; and a fluted portion proximate the distal end of the shaft, the fluted portion being disposed between a shoulder and a flat-bottom milling tip, the flat-bottom milling tip being configured to penetrate a peri-acetabular area of a pelvis as the fluted portion is imparted with rotary motion.

According to another aspect of the present application, the acetabular drill pin comprises an elongated shaft having a proximal end and a distal end opposite thereof along a longitudinal axis of the shaft, the distal end being defined by a flat-bottom milling tip; a first depth marking positioned between about 57 mm and about 58 mm from the flat-bottom milling tip; a second depth marking positioned between about 72 mm and about 73 mm from the flat-bottom milling tip; a stop surface positioned between about 18 mm and about 20 mm from the flat-bottom milling tip; and a fluted portion proximate the distal end of the shaft, the fluted portion being disposed between the stop surface and the flat-bottom milling tip.

In accordance with still another aspect of the present application, a method for positioning an acetabular cup during a hip procedure is provided. In accordance with this aspect of the present disclosure, the method comprises the steps of: placing a first acetabular guide within an acetabulum; securing a drill sleeve to the first acetabular guide; providing two acetabular drill pins each comprising: an elongated shaft having a proximal end and a distal end opposite thereof along a longitudinal axis of the shaft; two depth markings positioned along the shaft a pre-defined distance from the distal end; and a fluted portion proximate the distal end of the shaft, the fluted portion being disposed between a shoulder and a flat-bottom milling tip configured to penetrate a peri-acetabular area of a pelvis; individually inserting the two acetabular drill pins into the peri-acetabular area of the pelvis through the drill sleeve; removing the drill sleeve and the first acetabular guide from the acetabulum while leaving the two acetabular drill pins inserted into the peri-acetabular area of the pelvis; advancing a second acetabular guide over the two acetabular drill pins; inserting an alignment pin into the second acetabular guide; and placing an acetabular cup into the acetabulum by positioning the long axis of a cup inserter substantially parallel to the alignment pin as the cup is placed into the acetabulum.

Still other objects and benefits of the application will become apparent from the following written description along with the accompanying figures.

BRIEF DESCRIPTION OF THE DRAWINGS

The above-mentioned aspects of the present application and the manner of obtaining them will become more apparent and the teachings of the present application itself will be better understood by reference to the following description of the embodiments of the present application taken in conjunction with the accompanying drawings, wherein:

FIG. 4a represents a close-up and partial internal perspective view of a portion of the two illustrative drill pins of FIG. 4 during a surgical hip procedure;

Figure 1:
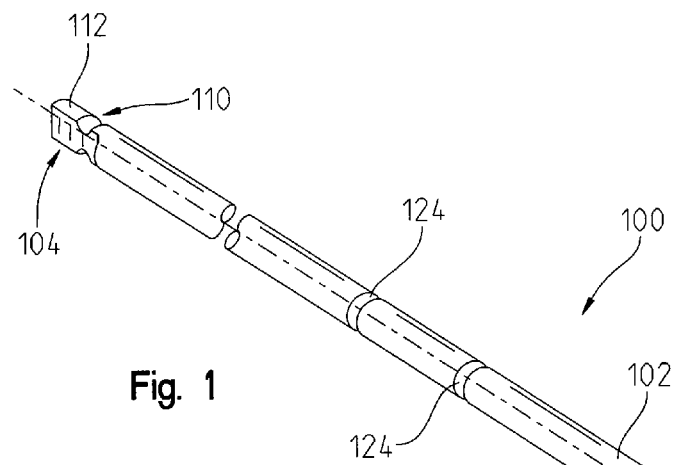
FIG. 1 represents a perspective view of an illustrative drill pin in accordance with the teachings of the present disclosure.

Corresponding reference characters indicate corresponding parts throughout the several views. Although the exemplification set out herein illustrates embodiments of the present application, in several forms, the embodiments disclosed below are not intended to be exhaustive or to be construed as limiting the scope of the present application to the precise forms disclosed.

DETAILED DESCRIPTION

The embodiments of the present application described below are not intended to be exhaustive or to limit the teachings of the present application to the precise forms disclosed in the following detailed description. Rather, the embodiments are chosen and described so that others skilled in the art may appreciate and understand the principles and practices of the present application.

Unless defined otherwise, all technical and scientific terms used herein have the same meaning as commonly understood by one of ordinary skill in the art to which this application belongs. Although any method and materials similar or equivalent to those described herein can be used in the practice or testing of the present application, the specific methods and materials are now described.

As described in commonly assigned U.S. Pat. No. 8,092,465, issued on Jan. 10, 2012, during a preoperative planning stage, imaging data of the relevant anatomy of a patient can be obtained at a medical facility or doctor's office. The imaging data can include, for example, a detailed scan of a pelvis, hip, knee, ankle or other joint or relevant portion of the patient's anatomy. The imaging data can be obtained using an MRI, CT, and X-Ray, ultrasound or any other imaging system. The imaging data obtained can be used to construct a three-dimensional computer image of the joint or other portion of the anatomy of the patient and prepare an initial pre-operative plan that can include bone or joint preparation, including planning for resections, milling, reaming, broaching, implant selection and fitting, design of patient-specific guides, templates, tools and alignment protocols for the surgical procedure.

Computer modeling for obtaining three-dimensional computer images of the relevant patient's anatomy can be provided by various CAD programs and/or software available from various vendors or developers. The computer modeling program can be configured and used to plan a preoperative surgical plan, including planning various bone preparation procedures, to select or design/modify implants and design patient-specific guides and tools including patient-specific prosthesis components, and patient-specific tools, including reaming, broaching, milling, drilling or cutting tools, alignment guides, templates and other patient-specific instruments.

The pre-operative plan can be stored in any computer storage medium, in a computer file form or any other computer or digital representation. The pre-operative plan, in a digital form associated with interactive software, can be made available via a hard medium, a web-based or mobile or cloud service, or a cellular portable device to the surgeon or other medical practitioner, for review. Using the interactive software, the surgeon can review the plan, and manipulate the position of images of various implant components relative to an image of the anatomy. The surgeon can modify the plan and send it to the manufacturer with recommendations or changes. The interactive review process can be repeated until a final, approved plan, is sent to a manufacturing facility for preparing the actual physical components.

After the surgical plan is approved by the surgeon, patient-specific implants and associated tools, including, for example, alignment guides, reaming or other tools for the surgical preparation of the joint or other anatomy portion of the specific patient can be designed using a CAD program or other three-dimensional modeling software according to the preoperative surgical plan. Patient-specific guides and other instruments can be manufactured by various stereolithography methods, selective laser sintering, fused deposition modeling or other rapid prototyping methods. In some embodiments, computer instructions of tool paths for machining the patient-specific guides and/or implants can be generated and stored in a tool path data file. The tool path data can be provided as input to a CNC mill or other automated machining system, and the tools and implants can be machined from polymer, ceramic, metal or other suitable material depending on the use, and sterilized. The sterilized tools and implants can be shipped to the surgeon or medical facility for use during the surgical procedure.

Patient-specific implants, guides, templates, tools or portions thereof are defined herein as those constructed by a surgical plan approved by the surgeon using three-dimensional images of the specific patient's anatomy and made to closely conform and mate substantially as a negative mold or negative surface or inverse or mirror surface of corresponding surface portions of the patient's anatomy, including bone surfaces with or without associated soft tissue, such as articular cartilage, for example, depending on the particular procedure, implant and tool use.

Patient-specific alignment guides and implants are generally configured to match the anatomy of a specific patient and can fit in only one position on a corresponding surface of the specific patient because anatomic features that are unique to each patient function as landmarks and can guide placement of the alignment guide or implant in only one position without the need of intraoperative navigation, patient marking or other intraoperative guidance. The patient-specific alignment guides are generally configured and manufactured using computer modeling based on the patient's 3-D anatomic image and have an engagement surface that is made to conformingly contact and match as a mirror or negative or inverse surface to a corresponding surface of a three-dimensional image/model of the patient's bone surface (with or without cartilage or other soft tissue), by the computer methods discussed above. The patient-specific alignment guides can include custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting pins or other fasteners according to a surgeon-approved pre-operative plan. The patient-specific alignment guides can be used in minimally invasive surgery, and also in surgery with multiple minimally-invasive incisions. Various alignment guides and pre-operative planning procedures are disclosed in commonly assigned U.S. Pat. No. 8,092,465, issued on Jan. 10, 2012, U.S. patent application Ser. No.

12/211,407, filed on Sep. 16, 2008; U.S. Pat. No. 8,070,752, issued on Dec. 6, 2011, U.S. Pat. No. 7,780,672, issued on Aug. 24, 2010; and U.S. Pat. No. 8,298,237, issued on Oct. 30, 2012. The disclosures of the above applications are incorporated herein by reference.

Figure 1A:
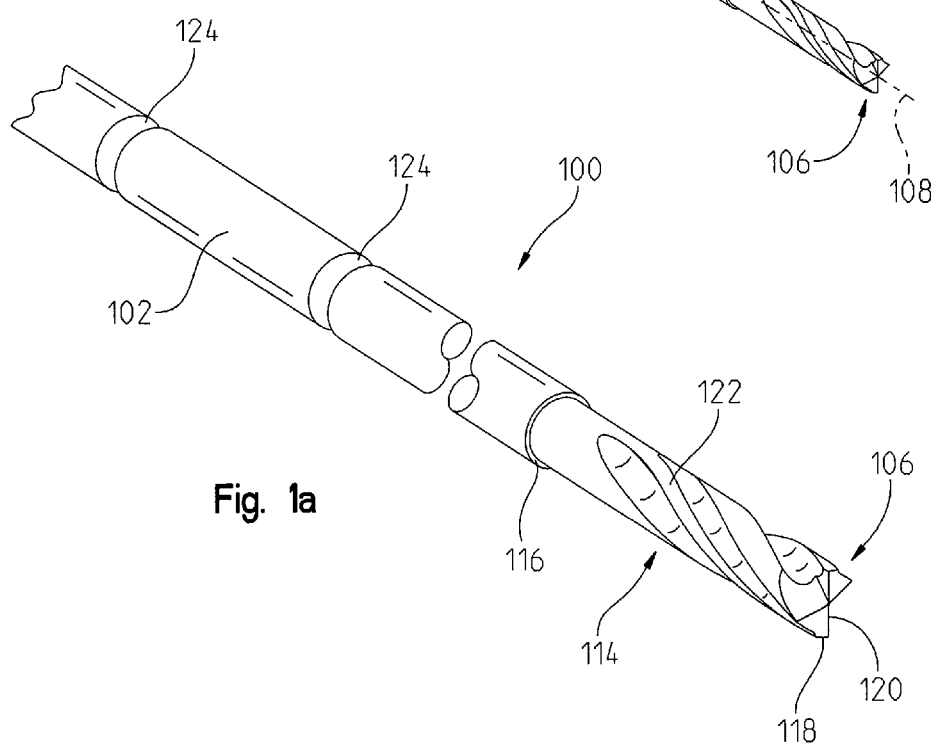
FIG. 1A represents a close-up view of the tip portion of the illustrative drill pin of FIG. 1.

Referring to FIGS. 1 and 1a, an acetabular drill pin 100 is provided in accordance with certain aspects the present teachings. According to this embodiment, the drill pin 100 comprises an elongated shaft 102 having a proximal end 104 and a distal end 106 opposite thereof along a longitudinal axis 108 of the drill pin 100. The proximal end 104 of the elongated shaft 102 comprises a drive shank portion 110 which terminates in a drive attachment post 112 that is configured to releasably couple with the chuck of a corresponding orthopedic drill that is designed to impart rotary motion to the drill pin 100. While this attachment can be achieved through any mechanical means know within the art, in accordance with certain aspects of the present disclosure, the drive attachment post 112 can be attached to the drill through an attachment means including, but not limited to, a press-fit or friction-fit engagement, a conventional Hudson connection, a square-drive quick-connection, a conventional drill chuck mechanism, a set screw, a tool clamp, a magnetic connection, a rivet, a snap ring, or the like. As such, it should be appreciated and understood herein that one skilled in the art would readily be able to recognize that the present teachings encompass any known attachment means and that the attachment choice will depend on the intended use of the drill pin 100.

To penetrate the peri-acetabular area of a pelvis (i.e., the area around the acetabulum), the distal end 106 of the drill pin's elongated shaft 102 has a fluted portion 114 disposed between a shoulder 116 and a cutting edge 118. While the cutting edge of many traditional drill pins comprise trocar tips, in accordance with certain aspects of the present disclosure, the cutting edge 118 of the fluted portion 114 utilizes an end-cutting, flat-bottom milling tip 120 that is designed to prevent surface deflection as the tip 120 encounters the peri-acetabular area of the pelvis during a surgical procedure.

The shoulder 116 is positioned a pre-determined distance from the milling tip 120 and is designed to function as a stop surface by providing a means for generating tactile feedback to the surgeon when the shoulder 116 encounters the outer surface of the pelvis. While the exact distance of the shoulder 116 from milling tip 120 may be adjusted without straying from the teachings of the present disclosure, in accordance with certain aspects of the present disclosure, the shoulder 116 is between about 18 mm and about 20 mm from the tip 120, and more specifically about 19 mm from the tip. As the shoulder 116 contacts the bone and the tactile feedback is generated, the surgeon then knows that the continued penetration of the drill pin 100 into the bone should be ceased; otherwise, damage to the patient's internal organs may be caused if the tip 120 is advanced through the inner cortex of the pelvis.

The fluted portion 114 includes a plurality of flutes 122 that aid in the removal of debris as the pin is advanced into the peri-acetabular area of the pelvis, as well as promotes the smooth advancement of the drill pin 100 into the bone. While those of skill in the art will understand and appreciate that the fluted portion 114 may have various different shapes depending on the use of the drill pin 100, in accordance with certain aspects of the present disclosure, the fluted portion 114 may have a cylindrical or frustoconical shape. Moreover, it should also be understood and appreciated herein that the size, orientation and number of flutes 122 defining the fluted portion 114 can be adjusted as necessary without straying from the teachings of the present disclosure, and particularly depending on the intended application and use of the drill pin 100. According to certain specific aspects of the present teachings, however, the fluted portion 114 may be shaped into a helical pattern and include between about 2 and about 6 flutes 122.

Along the elongated shaft 102 of the drill, in accordance with certain embodiments, at least one depth marking 124 may be added to provide a visual indication of how far the drill pin 100 has penetrated the acetabular surface of the pelvis. To accomplish this, the one or more depth markings 124 are positioned along the shaft 102 at a pre-determined distance from the tip 120. According to one specific embodiment herein, two depth markings 124 are included on the elongated shaft 102. In accordance with this specific embodiment, the two depth markings 124 are separated from each other by about 15 mm, with one of the depth markings being between about 57 mm and 58 mm from the tip 120, and the other depth marking being between about 72 mm and 73 mm from the tip.

While the drill pin 100 can be manufactured from any known surgical quality metallic component, in accordance with certain aspects of the present disclosure, the drill pin is made from a material including, but not limited to, stainless steel, titanium, aluminum, brass, cobalt chrome molybdenum alloys, nitinol alloys and the like.

Referring now to FIGS. 2-9, an illustrative surgical technique utilizing the above-described drill pin is provided. Before describing the surgical technique in detail, it should be understood that the anatomy of the patient can be initially prepared by removing as much soft tissue in and around the acetabulum as needed to allow for good exposure and fit for the acetabular guide components. To accomplish this, the labrum and soft tissue is removed from the rim of the acetabulum in areas of guide registration, as well as any fatty tissue in and around the acetabular fossa.

Figure 2:
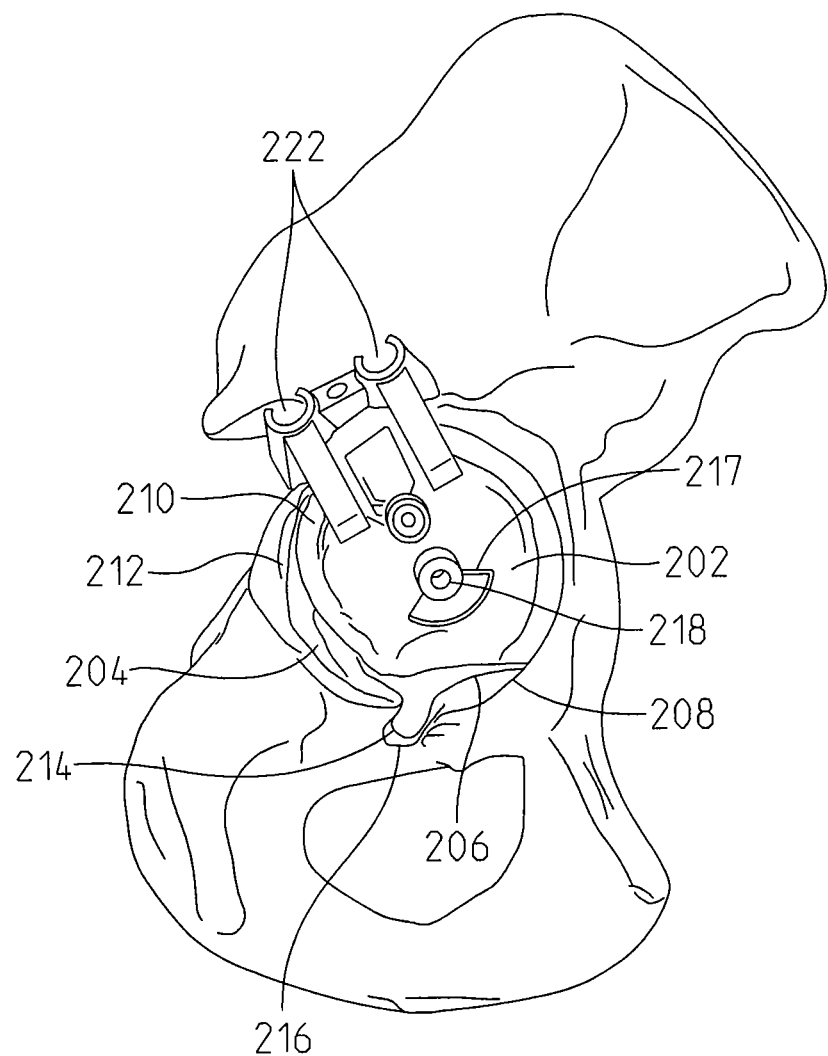
FIG. 2 represents a perspective view of a primary acetabular guide placed within a patient's acetabulum during a surgical hip procedure.

As shown in FIG. 2, once the soft tissue is removed, a patient-matched primary acetabular guide 202, which has been designed and produced to replicate the preoperative surgical plan, is placed into the native acetabulum 204. If desired, various design features of the acetabular guide 202 can be visually referenced intraoperatively with respect to the acetabulum 204 to confirm proper alignment. More specifically, a line 206 scribed on the inferior side of the guide 202 should be positioned substantially parallel to the transverse acetabular ligament 208, while the posterior edge of the guide 210 should be flush with the rim 212 of the acetabulum 204. Finally, a hook 214 on the inferior side of the guide should be locked into the posterior side of the acetabular notch 216, which is beneath the transverse acetabular ligament 208. The guide 202 may be further machined with one or more windows 217 that may also be used to visually confirm proper anatomical placement within the acetabulum.

While not shown herein, to aid with the placement of the guide 202 within the acetabulum 204, a guide inserter handle can be assembled to the central post 218 of the guide 202. Once assembled, the guide handle can be internally rotated while applying a light downward pressure with the handle to achieve proper guide registration.

Figure 3:
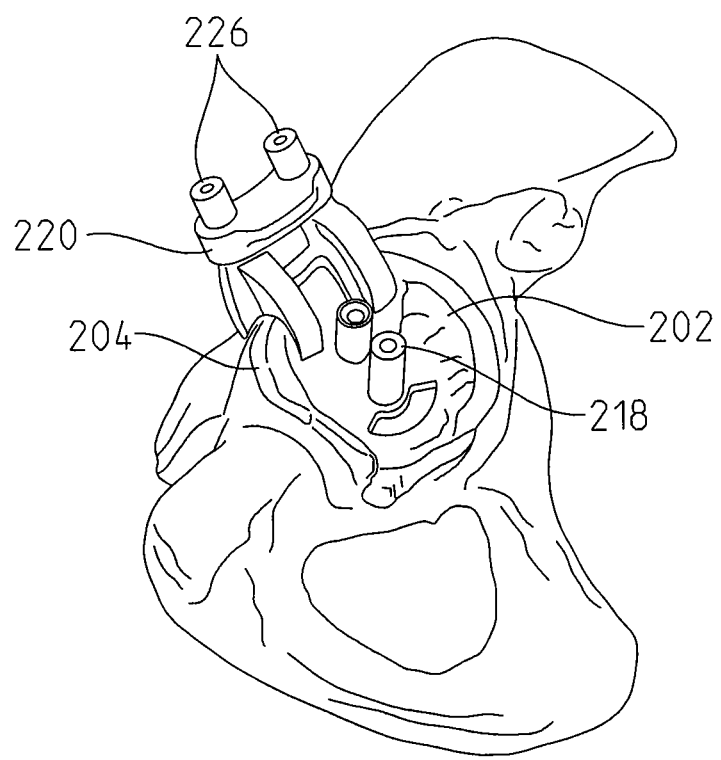
FIG. 3 represents a perspective view of a drill sleeve associated with the primary acetabular guide of FIG. 2 during a surgical hip procedure.
Figure 4:
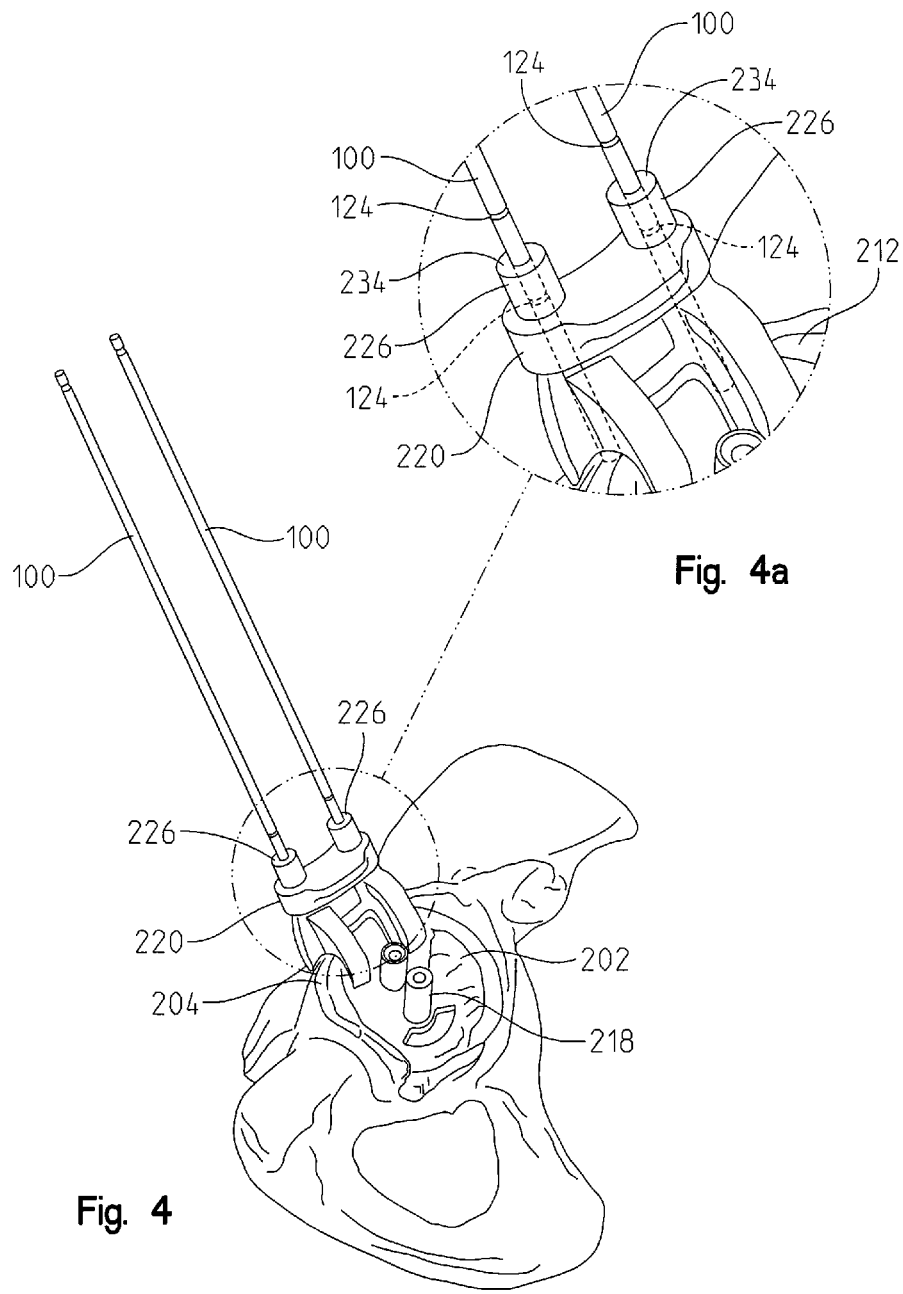
FIG. 4 represents a perspective view of two illustrative drill pins in accordance with the teachings of the present disclosure inserted into the drill sleeve of FIG. 3 during a surgical hip procedure.

Once the guide 202 is properly positioned within the acetabulum 204, as shown in FIG. 3, a drill sleeve 220 is placed into the tapered holes 222 of the guide 202 until a secure engagement is achieved. As is shown in FIGS. 4 and 4a, two drill pins 100 are individually advanced through respective guide hole ports 226 that extend from the drill sleeve 220 to thereby secure the guide 202 to the acetabulum 204, and particularly the per-acetabular area of the pelvis. To advance the drill pins 100 through the guide hole ports 226, a pin driver attached to a surgical drill can be used (not shown).

As shown in FIG. 4a, each of the pins 100 are drilled into the rim 212 of the acetabulum 204 until they are respectively seated to a depth as indicated by two depth markings 124 etched into the shafts of the pins. More particularly, as shown in FIG. 4a, in accordance with certain aspects of the present teachings, the drill pins 100 should be advanced into the acetabulum 204 until a top surface 234 of the guide hole port 226 is positioned approximately half-way between the two depth markings 124. While not required herein, in accordance with certain aspects of the present disclosure, the most anterior of the drill pins may be inserted first to secure the guide 202 in place and to aid with the insertion of the second pin. Despite the order to which the pins are inserted, it should be understood and appreciated herein that malpositioning the guide 202 during the insertion process may lead to malpositioning the final acetabular component. In addition, caution must be used when placing the drill pins to prevent soft tissue injury that may occur from penetrating the medial cortex of the pelvis. As is explained above, the drill pins of the present disclosure have been specifically designed to provide the surgeon with tactile feedback when the pin shoulder contacts the outer, lateral cortex of the pelvis. As such, excessive downward pressure should be avoided when drilling to prevent advancing the pin beyond its shoulder stop.

Figure 5:
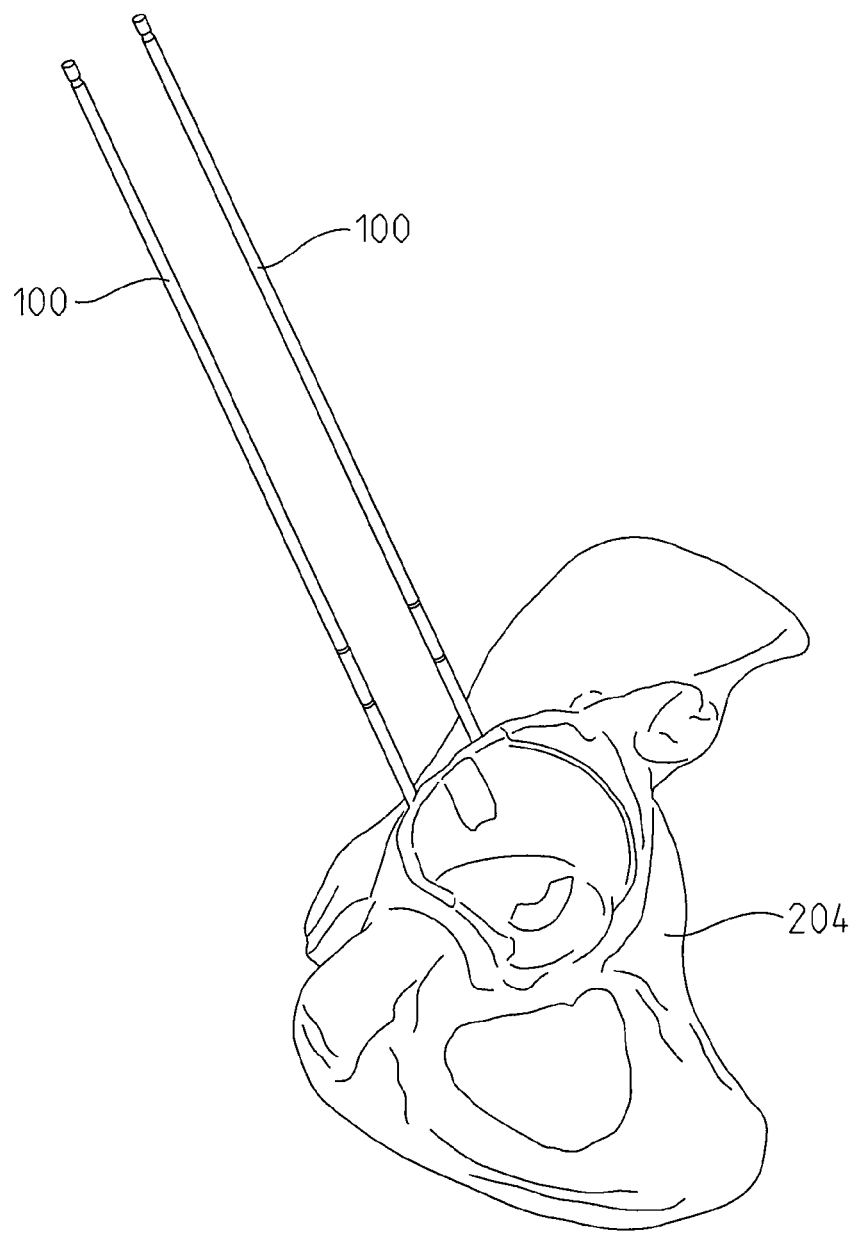
FIG. 5 represents a perspective view of the two drill pins of FIG. 4 inserted into the peri-acetabular area of a pelvis after the primary acetabular guide and drill sleeve have been removed during a surgical hip procedure.
Figure 6:
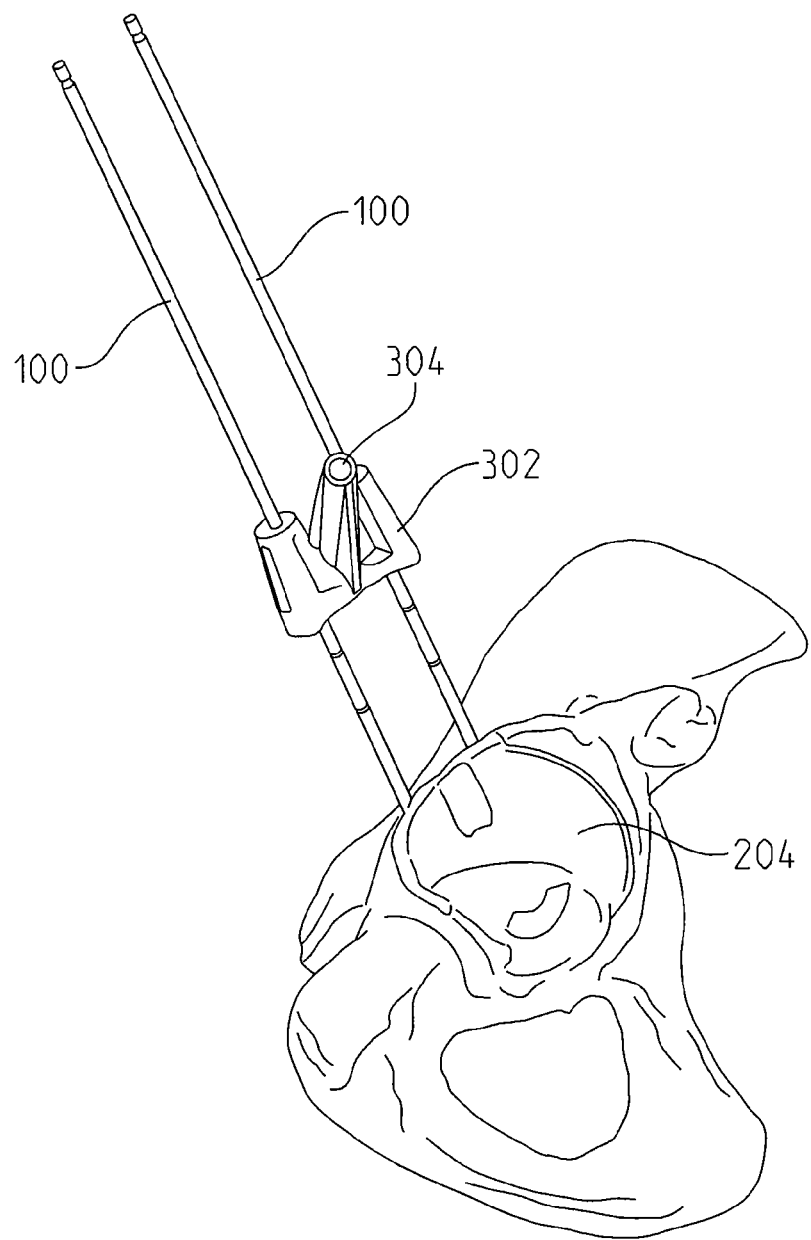
FIG. 6 represents a perspective view of a secondary acetabular guide positioned over the two illustrative drill pins of FIG. 4 during a surgical hip procedure.

As shown in FIG. 5, while leaving the drill pins 100 in place, the drill sleeve 220 is then removed and the guide 202 slid off the pins. A secondary acetabular guide 302 is then advanced over the drill pins 100 into a position such that the guide 302 does not obstruct the acetabulum 204 from being reamed as needed (see FIG. 6). In other words, it is not necessary that the guide 302 be seated or pushed all the way against the acetabulum 204. Moreover, the guide 302 should be positioned so that the alignment pin cylinder 304 of the guide protrudes away from the acetabulum 204.

Figure 7:
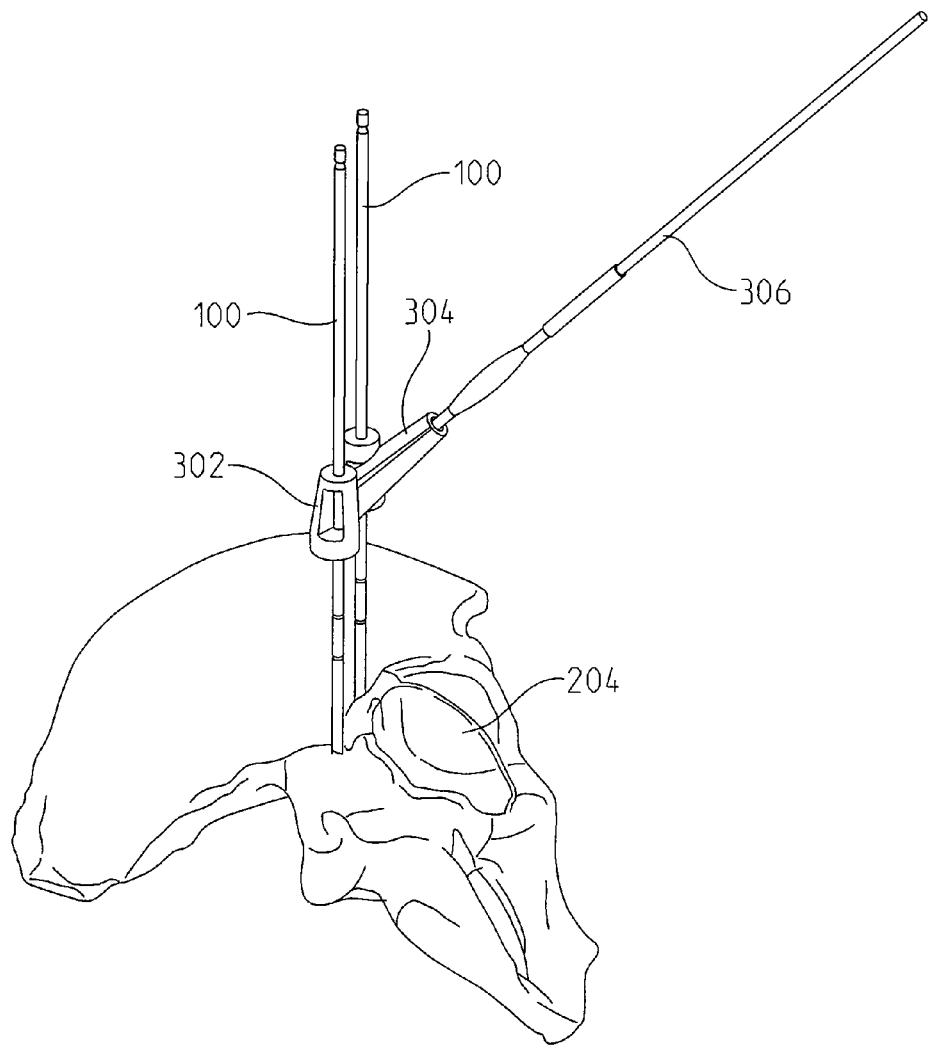
FIG. 7 represents a perspective view of an alignment pin inserted into the secondary acetabular guide of FIG. 6 during a surgical hip procedure.
Figure 8:
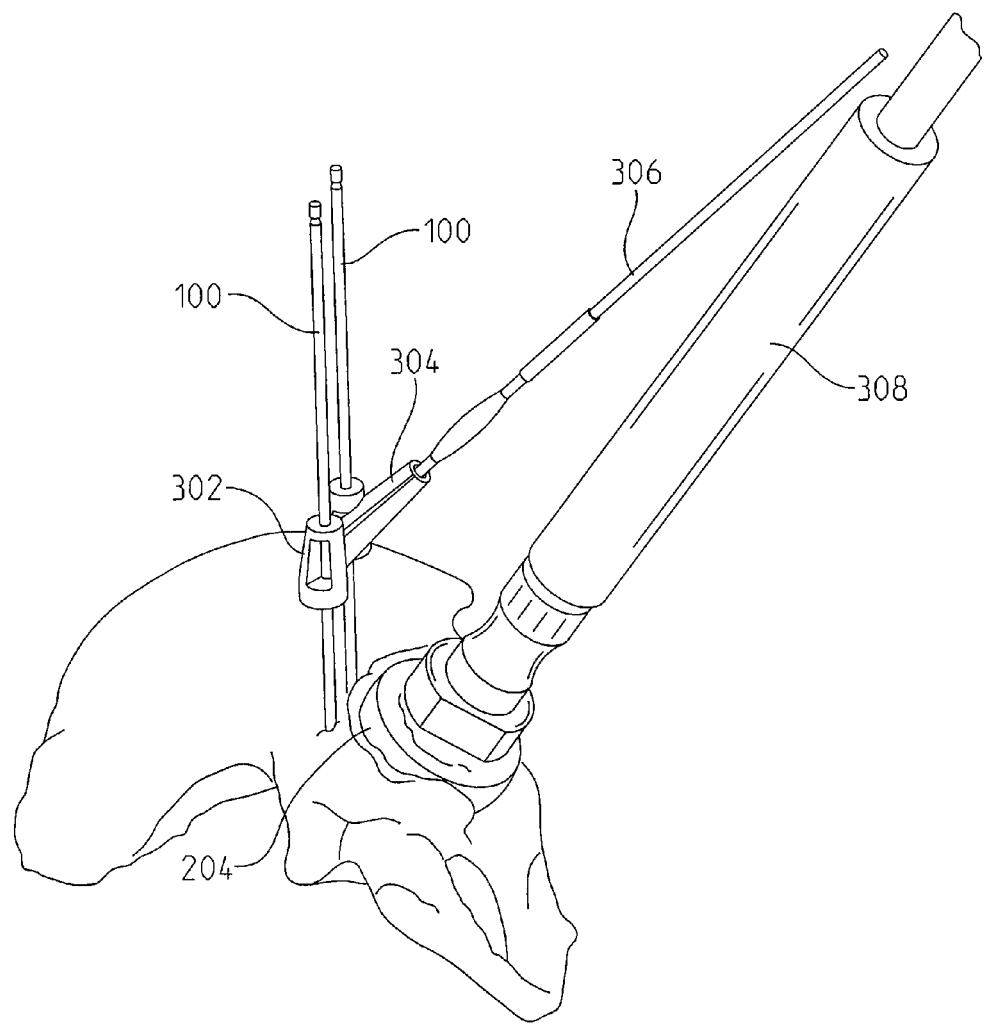
FIG. 8 represents a perspective view of the acetabulum being reamed during a surgical hip procedure.

As shown in FIG. 7, an alignment pin 306 is then inserted into the alignment pin cylinder 304 of the guide. While the alignment pin 306 should be oriented such that it is substantially parallel to the preoperatively planned cup insertion axis, the pin 306 does not need to be drilled into the bone, as it is used solely for alignment purposes.

After the alignment pin 306 has been inserted into the alignment pin cylinder 304, the surgeon then proceeds with reaming the acetabulum 204. While any surgical reaming technique preferred by the operating surgeon can be implemented in accordance with the teachings of the present disclosure, in accordance with certain aspects herein, a reaming device having an elongated handle 308 is used to ream the acetabular surface (see FIG. 8). While the alignment pin 306 may be used as a visual reference during the reaming process, reaming in alignment with the pin is not required and should not affect the final implant positioning in accordance with the present teachings. Moreover, it should be understood and appreciated herein that the secondary acetabular guide 302 may be repositioned at any point along the length of the drill pins or removed entirely during the reaming process if necessary.

Figure 9:
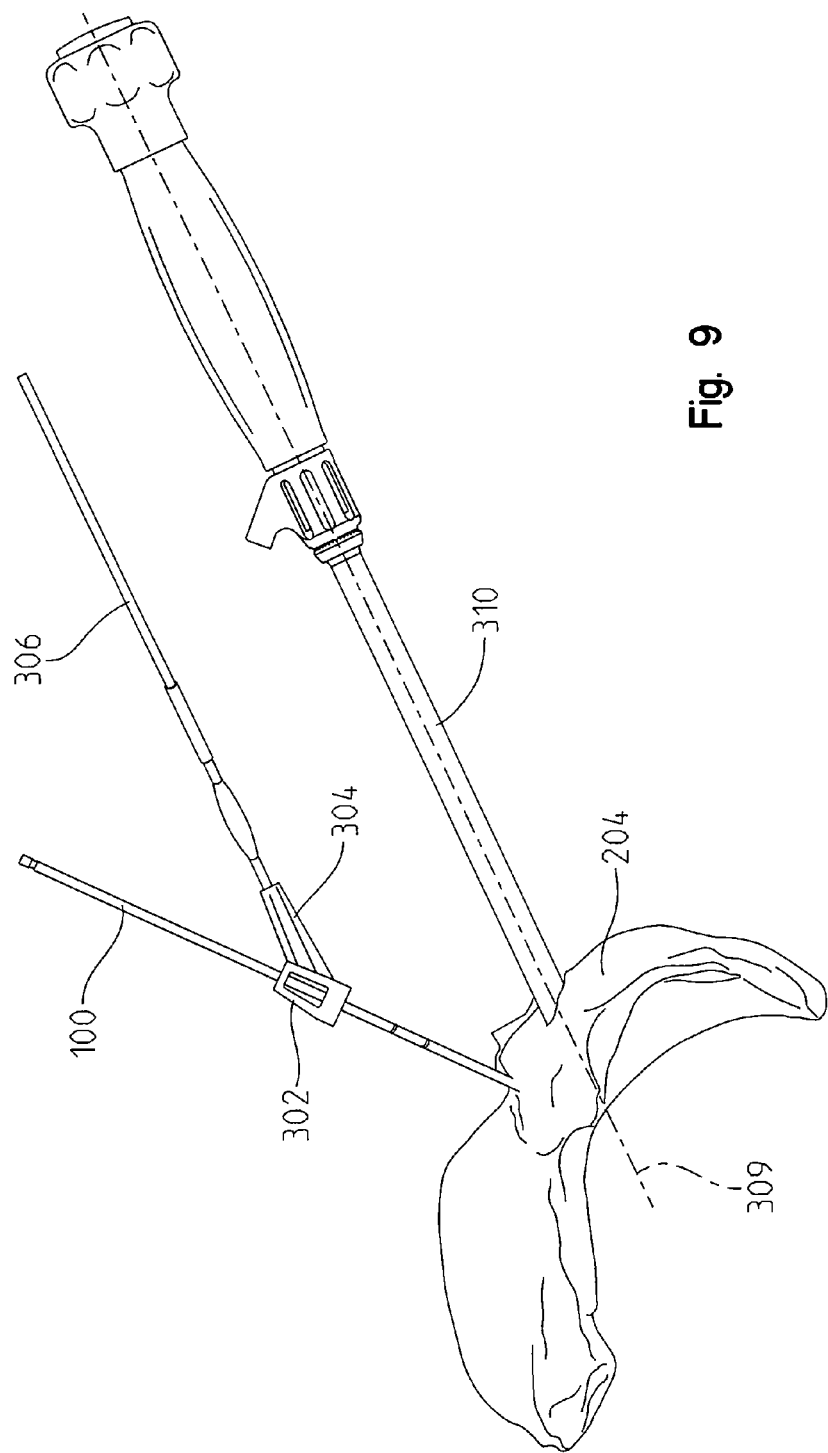
FIG. 9 represents a perspective view of an acetabular cup being inserted into the acetabulum during a surgical hip procedure.

After the acetabulum has been satisfactorily reamed, an acetabular cup is then inserted into the acetabulum 204. Before impacting the cup in accordance with the present teachings, as shown in FIG. 9, the long axis 309 of the cup inserter 310 should be oriented substantially parallel to the alignment pin 306. Once positioned appropriately, the handle of the cup inserter 310 is struck with a mallet while keeping the inserter steadily aligned with the alignment pin 306 until the cup is fully seated within the acetabulum. Thereafter, the cup inserter 310 can be removed, as well as the secondary guide 302 and drill pins 100.

While not shown herein, in accordance with certain alternative aspects of the present disclosure, an alignment pin adaptor can also be used during the cup insertion process to help keep the cup inserter 310 positioned substantially parallel to the alignment pin 306. In accordance with this aspect of the present disclosure, the alignment pin adaptor is attached to a guide on the cup inserter 310. The secondary guide 302 is then slid down the drill pins 100 until the alignment pin 306 contacts a groove on the alignment pin adaptor. During this process, it should be verified that the alignment pin 306 contacts the entire length of the groove in the alignment pin adaptor and that the long axis of the cup inserter 310 is substantially parallel to the alignment pin 306.

While an exemplary embodiment incorporating the principles of the present application has been disclosed hereinabove, the present application is not limited to the disclosed embodiments. Instead, this application is intended to cover any variations, uses, or adaptations of the application using its general principles. Further, this application is intended to cover such departures from the present disclosure as come within known or customary practice in the art to which this present application pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on", "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

What is claimed is:

1. A method for positioning an acetabular cup during a hip procedure, the method comprising the steps of: placing a first acetabular guide within an acetabulum; securing a drill sleeve to the first acetabular guide; providing two acetabular drill pins each comprising: an elongated shaft having a proximal end and a distal end opposite thereof along a longitudinal axis of the shaft; two depth markings positioned along the shaft a pre-defined distance from the distal end; and a fluted portion proximate the distal end of the shaft, the fluted portion being disposed between a shoulder and a flat-bottom milling tip configured to penetrate a peri-acetabular area of a pelvis; individually inserting the two acetabular drill pins into the peri-acetabular area of the pelvis through the drill sleeve; removing the drill sleeve and the first acetabular guide from the acetabulum while leaving the two acetabular drill pins inserted into the peri-acetabular area of the pelvis; advancing a second acetabular guide over the two acetabular drill pins; inserting an alignment pin into the second acetabular guide; and placing an acetabular cup into the acetabulum by positioning the long axis of a cup inserter substantially parallel to the alignment pin as the cup is placed into the acetabulum, wherein the step of individually inserting the two acetabular drill pins into the peri-acetabular area of the pelvis through the drill sleeve comprises drilling each of the acetabular drill pins into the peri-acetabular area of the pelvis until a top surface of the drill sleeve is positioned about half-way between the two depth markings of each acetabular drill pin.

2. The method of claim 1, further comprising the step of reaming the acetabulum after the alignment pin is inserted into the second acetabular guide.

3. The method of claim 1, further comprising the step of positioning the alignment pin substantially parallel to a pre-operatively planned acetabular cup insertion axis.

4. The method of claim 1, wherein the step of individually inserting the two acetabular drill pins into the peri-acetabular area of the pelvis through the drill sleeve comprises drilling each of the acetabular drill pins until the shoulder of the drill pin encounters the peri-acetabular area of the pelvis.

5. The method of claim 4, wherein the step of encountering the peri-acetabular area of the pelvis with the shoulder of the drill pin comprises physically contacting the shoulder with the peri-acetabular area of the pelvis to generate tactile feedback detectable by a surgeon performing the hip procedure.

6. The method of claim 1, further comprising the step of individually attaching the two acetabular drill pins to an orthopedic drill.

7. The method of claim 6, further comprising the step of individually imparting rotary motion on each of the two acetabular drill pins with the orthopedic drill to cause the flat-bottom milling tip of each drill pin to penetrate the peri-acetabular area of the pelvis.

\* \* \* \* \*